(12) United States Patent
Fourie et al.

(10) Patent No.: US 11,944,421 B2
(45) Date of Patent: Apr. 2, 2024

(54) MEDICAL NEEDLE

(71) Applicant: STELLENBOSCH UNIVERSITY, Stellenbosch (ZA)

(72) Inventors: Pieter Rousseau Fourie, Stellenbosch (ZA); Tys Van Der Merwe, Stellenbosch (ZA)

(73) Assignee: STELLENBOSCH UNIVERSITY, Stellenbosch (ZA)

( * ) Notice: Subject to any disclaimer, the term of this patent is extended or adjusted under 35 U.S.C. 154(b) by 761 days.

(21) Appl. No.: 17/044,917

(22) PCT Filed: Apr. 3, 2019

(86) PCT No.: PCT/IB2019/052714
§ 371 (c)(1),
(2) Date: Oct. 2, 2020

(87) PCT Pub. No.: WO2019/193507
PCT Pub. Date: Oct. 10, 2019

(65) Prior Publication Data
US 2021/0038112 A1 Feb. 11, 2021

(30) Foreign Application Priority Data
Apr. 3, 2018 (ZA) .................................. 2018/02103

(51) Int. Cl.
*A61B 5/00* (2006.01)
*A61B 5/0537* (2021.01)
(Continued)

(52) U.S. Cl.
CPC .......... *A61B 5/0537* (2013.01); *A61B 5/0086* (2013.01); *A61B 5/0538* (2013.01);
(Continued)

(58) Field of Classification Search
CPC .................................................... A61B 5/0537
See application file for complete search history.

(56) References Cited

U.S. PATENT DOCUMENTS 6,440,118 B2  8/2002  Burr
8,914,102 B1  12/2014  Rey
(Continued)

FOREIGN PATENT DOCUMENTS

WO    WO 2009/019707    2/2009

OTHER PUBLICATIONS

International Search Report and Written Opinion dated Jul. 18, 2019 by the International Searching Authority for International Application No. PCT/IB2019/052714, filed on Apr. 3, 2019 and published as WO 2019/193507 on Oct. 10, 2019 (Applicant-Stellenbosch University) (11 Pages).

*Primary Examiner* — Joseph M Santos Rodriguez
(74) *Attorney, Agent, or Firm* — Ballard Spahr LLP

(57) ABSTRACT

A needle is provided that has terminals located at or near its tip. The terminals are connectable to an impedance calculating circuit configured to enable the impedance calculating circuit to apply an alternating current input electrical signal to the terminals. The terminals are further configured to enable the impedance calculating circuit to measure a resultant electrical signal and calculate an impedance of biological tissue surrounding the tip. The needle may further include light transmitting media, that extends along the needle, and that is connectable to a light circuit. The light circuit may include an emitter/detector pair for transmitting light from the emitter, along the media, and emitting the light from the tip. A reflection of the emitted light may be transmitted from the tip to the detector and the light circuit may calculate the light absorption of the tissue.

13 Claims, 5 Drawing Sheets

(51) Int. Cl.
    *A61B 5/0538*    (2021.01)
    *A61B 17/34*    (2006.01)
    *A61M 5/158*    (2006.01)
    *A61B 17/00*    (2006.01)

(52) U.S. Cl.
    CPC ........ *A61B 5/6848* (2013.01); *A61B 17/3401* (2013.01); *A61M 5/158* (2013.01); *A61B 2017/00026* (2013.01); *A61M 2202/0464* (2013.01); *A61M 2202/048* (2013.01); *A61M 2205/587* (2013.01)

(56) References Cited

U.S. PATENT DOCUMENTS

| | | |
|---|---|---|
| 2011/0230906 A1 | 9/2011 | Modesitt |
| 2015/0057530 A1 | 2/2015 | Roggeveen |

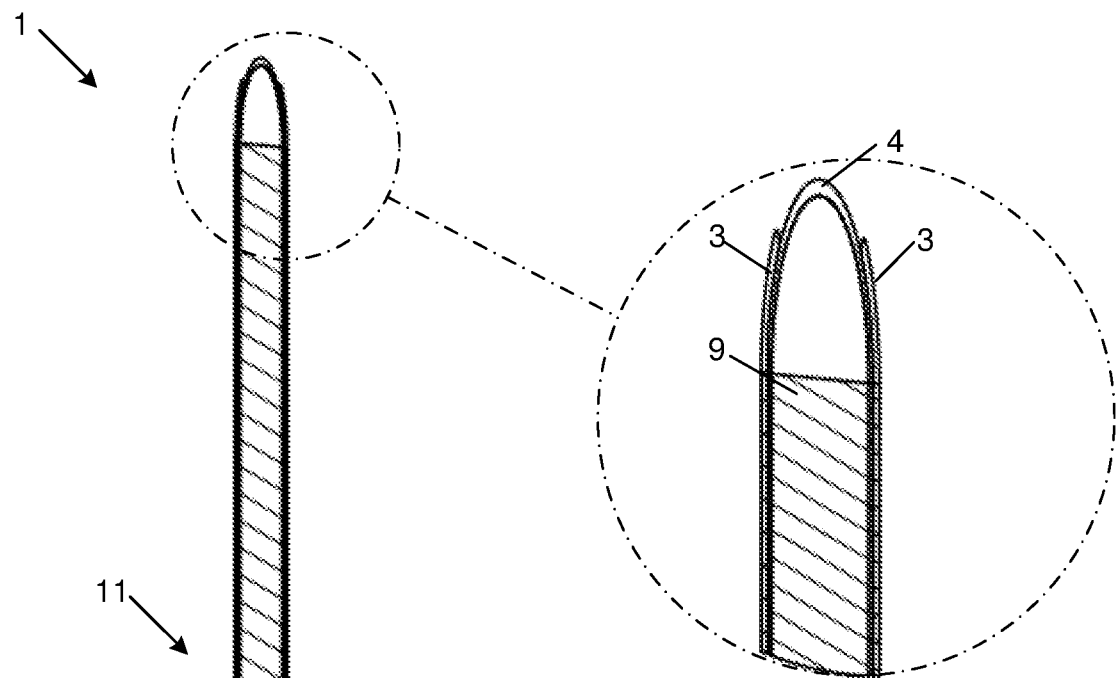
FIGURE 4
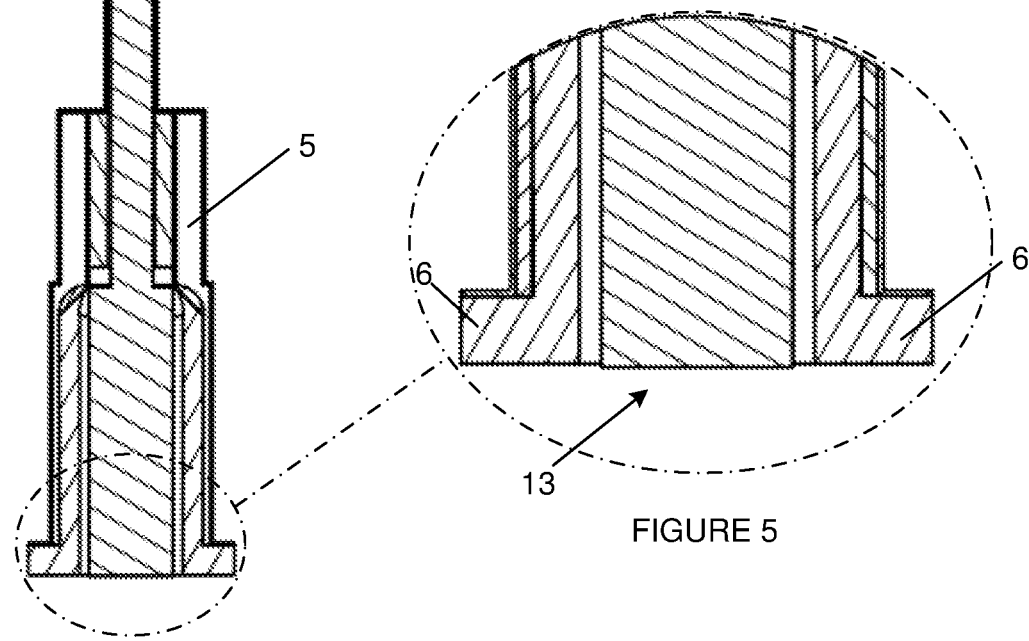
FIGURE 5
FIGURE 3

MEDICAL NEEDLE

CROSS-REFERENCE TO RELATED APPLICATIONS

This application is a U.S. National Phase Application of International Application No. PCT/IB2019/052714, filed Apr. 3, 2019, which claims priority to South African Application No. 2018/02103, filed Apr. 3, 2018, each of which are hereby incorporated by reference in their entirety.

FIELD OF THE INVENTION

This invention relates to medical needles and methods for utilising medical needles. It finds particular application in, but not limited to, medical procedures in which access to the spine or surrounding areas is required such as a lumbar puncture or the administering of epidural anaesthesia.

BACKGROUND TO THE INVENTION

A number of medical procedures require the physician to access blood vessels of the patient. Physicians typically rely on their practical experience and knowledge of the human anatomy to locate blood vessels. However, due to anatomical variations between patients, relying on experience and knowledge alone may in some cases be unreliable. The problem is exacerbated if the physician or nurse, as the case may be, is inexperienced as is often the case in teaching hospitals.

Other medical procedures involving the use of a needle includes using a needle in the spinal cord for administering epidural anaesthesia or performing a lumbar puncture, i.e. a medical procedure where a needle is inserted into the lower part of the spine to test for conditions affecting the brain, spinal cord or other parts of the nervous system. The procedure greatly relies on the experience and capability of the physician to locate the sub-arachnoid space, where cerebrospinal fluid (CSF) can be extracted from.

The extraction of CSF using a needle is particularly difficult because of the complexity of the number of layers the needle has to penetrate. The procedure is even more difficult when the needle length increases, as may be required for use with individuals who are overweight, for example. Often the needle either misses the spinal canal or ruptures a blood vessel causing blood to leak into the CSF, contaminating the sample and rendering the results unusable.

In certain emergency cases it is crucial to gain quick access to blood vessels for a number of reasons. During resuscitation, for example, it is very important to insert an intravenous (IV) line to quickly administer adrenaline. Moreover, procedures such as emergency blood transfusion and insertion of temporary pacemakers all require quick access to blood vessels.

In some patients, blood vessels may be more difficult to locate due to a particular medical condition or due to medical treatment they are undergoing, such as chemotherapy. In such cases, a physician or nurse may repeatedly attempt to locate a blood vessel, leading to additional discomfort and distress to the patient.

The Applicant believes there to be room for improvement.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with the invention there is provided a needle having terminals located at or near its tip that are connectable to an impedance calculating circuit and configured to enable the impedance calculating circuit to apply an alternating current input electrical signal to the terminals, the terminals further configured to enable the impedance calculating circuit to measure a resultant electrical signal and calculate an impedance of biological tissue surrounding the tip.

Further features provide for the needle to include light transmitting media extending along the needle that is connectable to a light circuit, the light circuit including an emitter/detector pair for transmitting light from the emitter, along the media, and emitting the light from the tip and for transmitting a reflection of the emitted light from the tip to the detector, wherein the light circuit is configured to calculate light absorption of the tissue.

Further features provide for the input electrical signal to be a constant current signal and for the resultant electrical signal to be a resultant voltage signal; and for the impedance calculating circuit to calculate the impedance of the biological tissue surrounding the tip using the constant current signal value and the a measurement of the resultant voltage using Ohm's law.

Further features provide for the impedance calculating circuit to be configured to determine a real and imaginary value of the calculated impedance; and configured to determine a magnitude and phase angle of the calculated impedance.

Further features provide for the emitter/detector pair to respectively emit and detect infra-red light, and for the light circuit to be configured to calculate infra-red light absorption of the tissue.

Further features provide for the impedance calculating circuit to be configured to determine the type of biological tissue from either or both of the calculated impedance and the calculated light absorption of the tissue; and for the determined tissue to be selected from the group consisting of fat, muscle, blood, and cerebrospinal fluid.

Further features provide for the frequency of the alternating current input electrical signal to be between 10 kHz and 50 kHz, preferably between 25 kHz and 35 kHz, and more preferably between 28 kHz and 32 kHz.

Further features provide for the terminals to terminate at base of the needle; for the base to include two exposed connections to the terminals; for the base to be provided with a Luer lock fitting; and for the impedance calculating circuit to be provided with a complementary fitting to the Luer lock fitting of the base.

Embodiments of the invention will now be described, by way of example only, with reference to the accompanying drawings.

BRIEF DESCRIPTION OF THE DRAWINGS

In the drawings:

FIG. 3 is a cross-sectional view along the line II-II shown in FIG. 2;

FIG. 4 is an enlarged view of a tip of the needle of FIG. 3;

FIG. 5 is an enlarged view of a base of the needle of FIG. 3;

DETAILED DESCRIPTION WITH REFERENCE TO THE DRAWINGS

Figure 1:
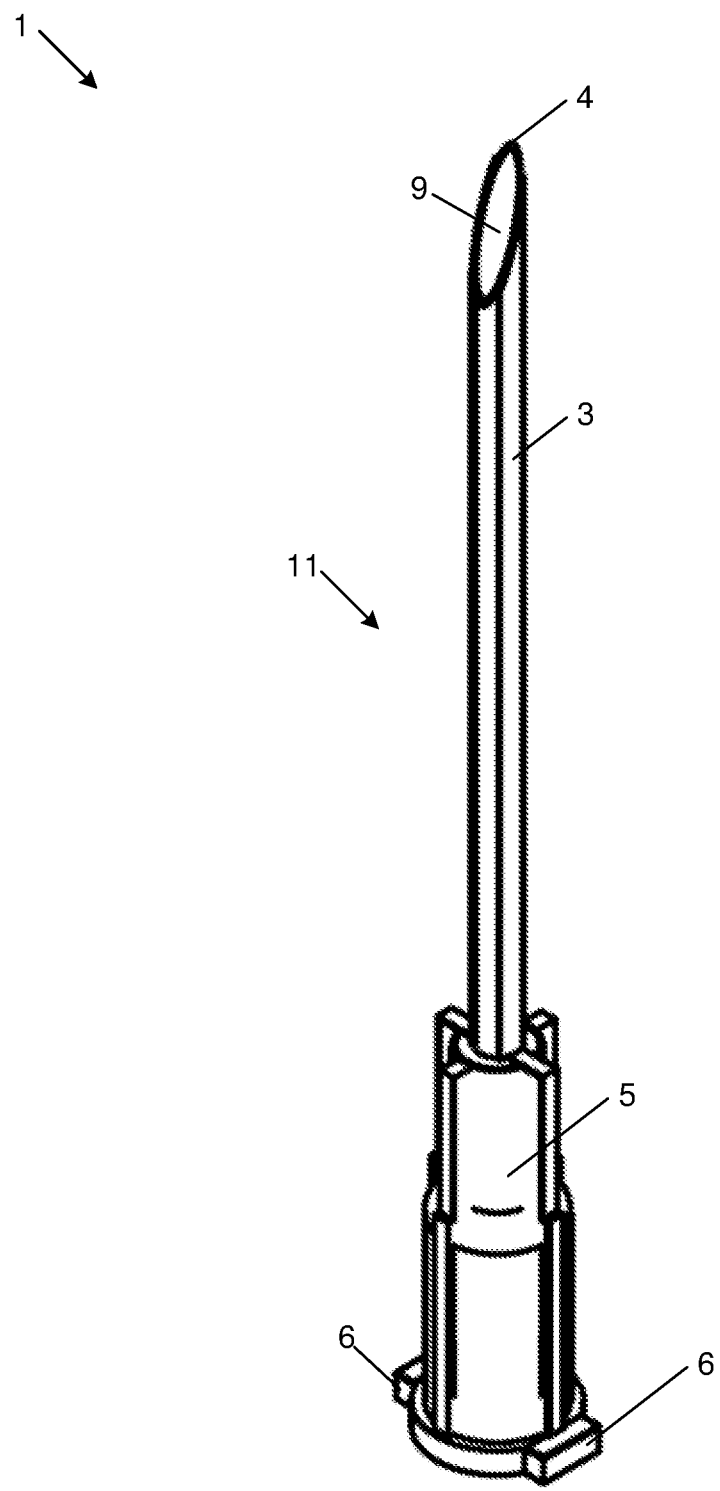
FIG. 1 is a three-dimensional view of a needle in accordance with the invention.
Figure 2:
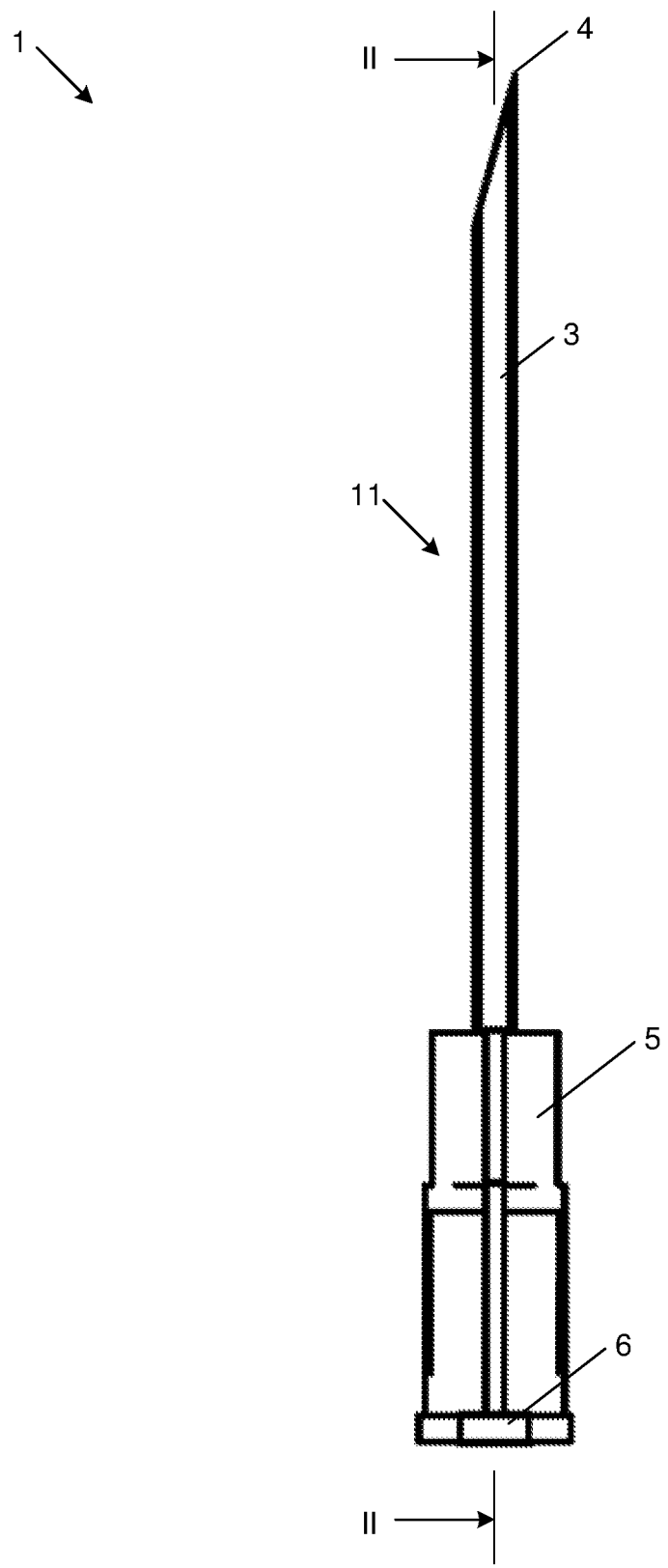
FIG. 2 is an elevation of the needle of FIG. 1.

FIGS. 1 to 6 show an embodiment of a medical needle. The needle (1) has at least two electrodes or terminals (3) located at or near its tip (4) that may terminate at a hub or base (5) of the needle for connection to an impedance calculating circuit, as will be described in more detail further below. The base (5) of the needle (1) may be provided with a Luer lock fitting (6). As shown more clearly in FIG. 6, the Luer lock fitting (6) of the needle may be configured to mate with a cooperating fitting (7) provided by a housing (8) of the circuitry (10).

Figure 6:
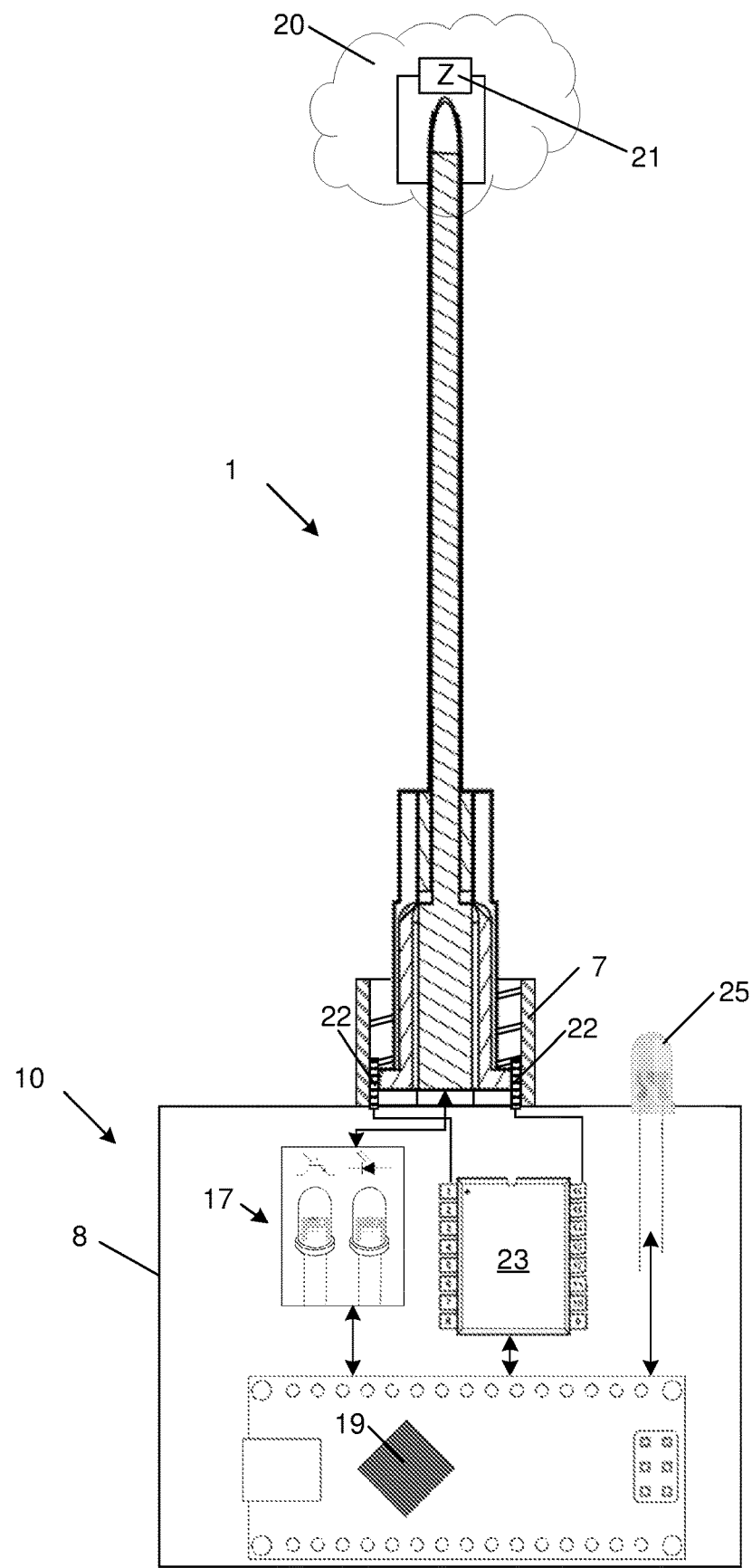
FIG. 6 shows the needle of FIG. 1 in use with exemplary light circuitry and impedance circuitry with a tip of the needle inserted in biological tissue.

The needle (1) may furthermore have light transmitting media (9) that extends axially within the shaft (11) of the needle (1). In one embodiment, the light transmitting media (9) may be one or more optic fibres extending axially within the needle (1). However, in the embodiment shown in the Figures, the light transmitting media (9) is an optically conductive resin that extends axially within the shaft (11) of the needle, from the base (5) to the tip (4). The base-end (13) of the light transmitting media (9) is connectable to a light circuit, as shown in FIG. 6, that includes an emitter/detector pair (17), for example an infra-red (IR) emitter/detector pair. The emitter of the emitter/detector pair (17) is configured to transmit light, to conduct the light along the light transmitting media (9), and to allow the light to be emitted from the tip (4). Light reflections (caused by this light emission) are transmitted from the tip (4) of the needle (1), through the light transmitting media (9), to the detector of the emitter/detector pair (17).

The light circuit may be in communication with a processor (19) configured to calculate the light absorption of the tissue (20) in the direction that the needle tip (4) points and to determine the type of this tissue by comparing it to known light absorption characteristics of a number of tissue types. For example, when the emitter (17) is directed toward a blood vessel, less infra-red light may be reflected and thus detected by the detector as a result of infra-red light absorption by haemoglobin in the blood of the relevant blood vessel. The processor (19) may process the lower output of the detector (due to the absorption of the light emitted by the emitter) and determine that the needle (1) is directed toward a particular type of biological tissue, such as a blood vessel. This may be indicated to a user by an indicator (25) as discussed further below.

When the base (5) of the needle is secured in the Luer lock fitting (7) of the circuitry housing (10), a pair of cooperating exposed contacts or cooperating terminals (22) makes contact with the terminals (3) of the needle (1) to electrically connect the terminals (3) with the impedance calculating circuit. The impedance calculating circuit may apply a known voltage to the terminals (3). By measuring the resulting current, the impedance (21) of the tissue (20) that surrounds the terminals (and thus the tip of the needle) may be calculated.

Preferably, the impedance calculating circuit injects a constant current source into the surrounding tissue via the terminals (3) and measures the resulting voltage across the terminals. The bioimpedance, that is the impedance of the biological tissue, may then be calculated using these two known values. It is generally preferable to inject a current and measure the resulting voltage, rather than applying a voltage and measuring the resulting current to measure bioimpedance since it is safer for the patient to inject a controlled current. It also allows the signal to noise ratio of the measurement signals to be optimised, since the current source may inject a prescribed maximum safe current.

The impedance calculating circuit may include an impedance converter (23) provided in an integrated circuit, such as the AD5933 manufactured by Analog Devices. The impedance converter (23) may apply a frequency sweep across a frequency range to determine the impedance value at various frequencies (see FIG. 7). The impedance converter may provide a real and imaginary part of each of the impedance values (thus at each of the various frequencies) as output to the processor (19). The processor (19) may convert these real and imaginary parts of the impedance values to a magnitude and phase angle as shown in FIG. 7.

In other embodiments, each of the impedance calculating circuit, the light circuit and the processor may comprise analogue circuitry.

However, it is further envisaged that the impedance converter (23) may be configured to select a particular frequency for its input signal, i.e. the injected current, at which the impedance and/or phase angle between various tissue types may be particularly distinguishable. In FIG. 7, for example, an initial characterisation of blood, muscle and fat tissue impedance was determined by inserting the tip (4) of the needle (1) into the relevant tissue and performing a number of frequency sweeps, resulting in the discrete areas displayed on the graphs. From the results shown in FIG. 7, the impedance converter (23) may, for example, be configured to use a frequency near 30 kHz, at which there is a distinct difference in the impedance magnitude as well as phase angle between the different tissues.

Figure 7:
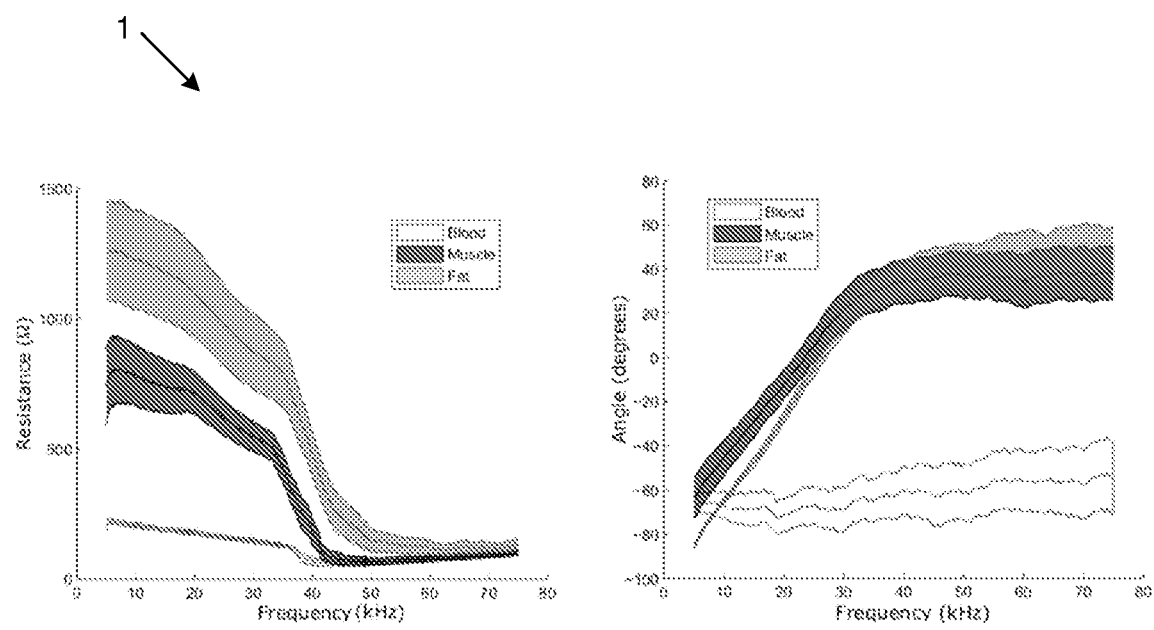
FIG. 7 is a graph showing exemplary impedance values of different tissue types.

The impedance calculating circuit may be configured to determine the type of tissue surrounding the needle tip by comparing it to known impedance characteristics of a number of tissue types (such as shown in FIG. 7).

The epidural space is a pseudo space consisting of fat tissue, blood vessels and a small amount of interstitial fluid. The combination of the impedance characteristics and light absorption may allow the epidural space to be located. An anaesthetic agent can then be injected into the space where it will attach to the nerves transecting the epidural space and thus produce the desired loss of sensation. This will allow the patient to be fully awake whilst a surgical procedure is carried out on the anaesthetised body component without affecting respiration.

In terms of electrical impedance, the impedance of the epidural space is very different from any other area in this vicinity, such as blood vessels and that of CSF. Thus, by performing a frequency sweep as explained above, the needle tip (where the impedance sensor's terminals are located) may be enabled to continuously map the area until such time that the impedance profile matches the impedance signature of the epidural space previously identified and stored on-board.

The needle (1) may therefore determine, in real-time, the type of tissue at a current position of the needle tip (4), as well as a tissue type that is located in the direction that the needle is pointing. This may determine where, anatomically speaking, the needle is situated and where the needle is headed. One may therefore also determine whether the needle is pointing in the desired direction, i.e. to reach the determined part of the anatomy should the needle be further inserted into the patient.

The needle may be a solid needle, since the light transmitting media (9) extends axially within the core of the needle. The needle may therefore be inserted with a coaxially fitted catheter (not shown). Once the physician has positioned the needle tip (4) in the desired anatomical position, the needle may be retracted to leave the catheter in place. The catheter may then provide subsequent access to administer anaesthesia or to collect CSF, for example.

It is envisaged that the needle may be disposable, and that the circuitry may include an indicator (25), such as a LED, to indicate when the needle tip (4) has made contact with the CSF. The indicator (25) may furthermore facilitate the directional movement of the needle until it points towards the CSF and away from any arteries.

The epidural space of a patient is of particular importance to an anaesthetist, who will often deposit a local pain killer in the epidural space for epidural anaesthesia. It is envisaged that the two sensors will synergistically aid to enable the anaesthetist to locate this space. The indicator (25) may be a multi-colour LED that indicates colour coded statuses to indicate the successful detection of both the epidural space and spinal canal.

The embodiment of the needle (1) described above utilises two electrodes and the pair of electrodes perform the duel functionality. Firstly, it provides a signal input function in which it applies a test voltage or injects a test current, as the case may be; and also a measurement function in which it conducts the resultant measurement current or voltage, as the case may be, to the circuitry for processing. It is envisaged that, in another embodiment, the needle may have four electrodes with a first pair of electrodes performing the input function, and the second pair performing the measurement function. The choice between two or four electrodes may depend, among other factors, on the frequency or frequency range of the input signal. When a lower frequency range is used, for example between 100 Hz and 20 kHz, four electrodes may be preferable and if a higher frequency range is used, say between 12 and 100 MHz, two electrodes may be preferable. However, these ranges are only examples and may depend on the particular application of the needle.

Furthermore, the needle (1) described above is provided with a Luer lock fitting (6). However, any fitting that allows the needle to form a fit with a complementary fitting of the housing may be used. The Luer lock may be preferable as that it is an industry standard fitting and provides a secure fitting to ensure the integrity of the connections between the needle and the light and impedance calculating circuits.

The invention therefore provides an apparatus enabling a user to receive continuous real-time feedback for determining a correct needle direction prior to penetrating tissue or at least after minimal penetration; and, after penetration, receiving continuous real-time feedback for determining the tissue layer at a current penetration depth.

The invention may present a number of further advantages. For example, the apparatus may assist physicians, EMT personnel and the like to access a blood vessel quickly, which is particularly advantageous in an emergency situation. It may furthermore assist in training of medical personnel whom, at least initially, would be inexperienced in locating blood vessels, the sub-arachnoid space, and the like, depending on the requirement of a particular medical procedure.

The foregoing description has been presented for the purpose of illustration; it is not intended to be exhaustive or to limit the invention to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon.

Finally, throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A needle comprising:
    terminals located at or near its tip that are connected to an impedance calculating circuit and configured to enable the impedance calculating circuit to apply an alternating current input electrical signal to the terminals, the terminals further configured to enable the impedance calculating circuit to measure a resultant electrical signal and calculate an impedance of biological tissue surrounding the tip;
    light transmitting media extending along the needle that is connected to a light circuit, the light circuit including an emitter/detector pair for transmitting light from the emitter, along the media, and emitting the light from the tip and for transmitting a reflection of the emitted light from the tip to the detector, wherein the light circuit is configured to calculate light absorption of the tissue; and
    wherein the impedance calculating circuit is configured to determine the type of biological tissue from both of the calculated impedance and the calculated light absorption of the tissue.

2. The needle as claimed in claim 1 wherein the input electrical signal is a configurable constant current signal and the resultant electrical signal is a resultant voltage signal.

3. The needle as claimed in claim 2 wherein the impedance calculating circuit is configured to calculate the impedance of the biological tissue surrounding the tip using the constant current signal value and a measurement of the resultant voltage using Ohm's law.

4. The needle as claimed in claim 1 wherein the impedance calculating circuit is configured to determine a real and imaginary value of the calculated impedance.

5. The needle as claimed in claim 1 wherein the impedance calculating circuit is configured to determine a magnitude and phase angle of the calculated impedance.

6. The needle as claimed in claim 1 wherein the emitter/detector pair is configured to respectively emit and detect infra-red light, and for the light circuit to be configured to calculate infra-red light absorption of the tissue.

7. The needle as claimed in claim 1 wherein the determined tissue is selected from the group consisting of fat, muscle, blood, and cerebrospinal fluid.

8. The needle as claimed in claim 1 wherein the frequency of the alternating current input electrical signal is selected to be between 10 kHz and 50 kHz.

9. The needle as claimed in claim 8 wherein the frequency of the alternating current input electrical signal is selected to be between 25 kHz and 35 kHz.

10. The needle as claimed in claim 8 wherein the frequency of the alternating current input electrical signal is selected to be between 28 kHz and 32 kHz.

11. The needle as claimed in claim 1 wherein the terminals terminate at a base of the needle and wherein the base includes exposed connections to the terminals.

12. The needle as claimed in claim 11 wherein the base is provided with a Luer lock fitting.

13. The needle as claimed in claim 12 wherein the impedance calculating circuit is provided with a complementary fitting to the Luer lock fitting of the base.

\* \* \* \* \*